United States Patent [19]

Reitz et al.

[11] 4,258,448

[45] Mar. 31, 1981

[54] METHOD OF DISPERSING, EMULSIFYING MATERIALS WITH PHOSPHORIC ACID ESTERS

[75] Inventors: Günther Reitz, Cologne; Günther Boehmke, Leverkusen; Karlhans Jakobs, Berg.-Gladbach, all of Fed. Rep. of Germany

[73] Assignee: Bayer Aktiengesellschaft, Leverkusen, Fed. Rep. of Germany

[21] Appl. No.: 915,019

[22] Filed: Jun. 13, 1978

[30] Foreign Application Priority Data

Jun. 15, 1977 [DE] Fed. Rep. of Germany ....... 2726854

[51] Int. Cl.³ .............................................. C09B 67/42
[52] U.S. Cl. .......................................... 8/582; 8/584; 8/907; 260/952; 260/978; 252/311; 252/312; 252/351; 252/356
[58] Field of Search ................. 260/978, 952; 8/89 R, 8/582; 352/311, 312, 351, 356

[56] References Cited

U.S. PATENT DOCUMENTS

| Re. 27,969 | 4/1974 | Camacho et al. | 260/952 |
| 2,891,985 | 6/1959 | Hurdis et al. | 260/952 |
| 3,022,330 | 2/1962 | Lanham | 8/89 |
| 3,544,614 | 12/1970 | Schwartz | 260/952 |
| 3,639,534 | 2/1972 | Reymore et al. | 260/952 |
| 3,689,532 | 9/1972 | Emmons et al. | 260/952 |

*Primary Examiner*—Anton H. Sutto
*Attorney, Agent, or Firm*—Sprung, Felfe, Horn, Lynch & Kramer

[57] ABSTRACT

Water-soluble phosphoric acid esters which are prepared from polyols and/or epoxides, in some cases polycarboxylic acids or their derivatives and phosphoric acids in the molar ratio 1:(0 to 1.5):(0.05 to 1.5), the sum of the numbers of mols of the carboxylic acids and phosphoric acids being 2/3 to 3/2 of the number of mols of the alcohols, can be used as dispersing agents, liquefaction agents, levelling agents and emulsifiers and builders in detergents.

9 Claims, No Drawings

METHOD OF DISPERSING, EMULSIFYING MATERIALS WITH PHOSPHORIC ACID ESTERS

The invention relates to water-soluble phosphoric acid esters which are prepared by reacting 1. (a) polyhydric saturated or unsaturated aliphatic, cycloaliphatic, aromatic or araliphatic alcohols which have 2 to 26 C atoms and optionally contain halogen, amino or sulpho groups, and/or
   (b) polyhydric alcohols which are formed by etherifying one or more of the compounds mentioned under 1.(a) with one another or by ethoxylating and/or propoxylating one or more of the compounds mentioned under 1.(a), and/or
   (c) 1,2-epoxide forms and 1,3-epoxide forms of the alcohols mentioned under 1.(a), and optionally
2. saturated or unsaturated aliphatic, cycloaliphatic, aromatic or araliphatic carboxylic acid which have 2 to 26 C atoms and contain at least two COOH groups, and may contain hydroxyl, ether, halogen, amino, sulpho or phosphonic acid groups, and functional derivatives thereof, for example anhydrides, acid halides or esters, and
3. phosphoric acid, its anhydride forms, for example phosphorus pentoxide, metaphosphoric acid, polyphosphoric acid with a $P_2O_5$ content of 73 to 100%, phosphoric acid halides or phosphoric acid oxyhalides.

The molar ratio of the compounds here is 1:(0 to 1.5):(0.05 to 1.5), and the sum of the numbers of mols of the compounds of groups 2 and 3 is ⅔ to 3/2, preferably ¾ to 4/3, of the number of mols of compounds of groups 1.

The invention also relates to the preparation of the phosphoric acid esters and their use as dispersing agents, liquefaction agents, levelling agents and emulsifiers and builders or sequestering agents for detergents.

Preferred compounds of group 1(a) and 1(b) have the formula $$HO—B—OH \qquad (I)$$

wherein
B denotes an alkylene or alkenylene radical with 2 to 10 C atoms, which can be substituted by 1 to 4 hydroxyl groups and/or can be interrupted by Z—N<
wherein
Z=$C_1$–$C_4$-alkyl which is optionally substituted by OH, and/or

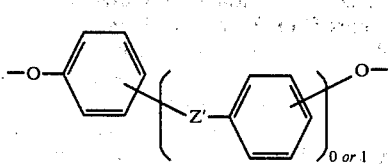

wherein
Z'=$SO_2$ or $C_1$–$C_3$-alkylene,
and/or by one of the isomeric phenylene or cyclohexylene radicals,
or represents one of the isomeric cyclohexylene radicals
or a radical of the formula

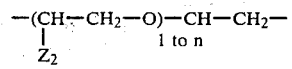

wherein
$Z_2$=H or $CH_3$ and
n=50, but preferably 20.

Preferred compounds of group 2 are acids of the formula $$HOOC—A—COOH \qquad (II)$$

their anhydrides, acid halides or esters.

In formula (II), A represents alkylene with 1 to 10 C atoms, alkenylene or alkinylene with 2 to 10 C atoms or one of the isomeric phenylene, biphenylene, cyclohexylene or norbornenylene radicals. These radicals can be substituted by $C_1$–$C_4$-alkoxy, sulphone or phosphonic acid groups.

Examples which may be mentioned of compounds of group 1 are: ethane-1,2-diol, propane-1,2-diol, propane-1,3-diol, butane-1,2-diol, butane-1,3-diol, butane-2,3-diol, butane-1,4-diol, 3-chloro-propane-1,2-diol, the individual isomeric petanediols, hexanediol, for example hexane-1,6-diol, and the individual isomeric diols of the higher alkanes. Unsaturated diols, such as 2-butene-1,4-diol, 2-hydroxy-methyl-2-propen-1-ol and alcohols which are more than dihydric, such as glycerol and trishydroxymethylalkanes, such as tris-hydroxymethyl-propane, and furthermore sugar alcohols, $C_{1-6}$-alkyldiethanolamines, $C_{1-6}$-alkyldiisopropanolamines, triethanolamine, triisopropanolamine and pentraaerythritol may also be mentioned. Aromatic and especially araliphatic alcohols may also be mentioned, such as the three isomeric bis-(2-hydroxyethoxy)-benzenes, and bis-(2-hydroxypropoxy)-benzenes, and furthermore, 4,4'-bis-(2-hydroxyethoxy)-dipehnyl sulphone, 4,4'-bis-(2-hydroxypropoxy)-diphenyl sulphone, the individual isomeric bis-(2-hydroxy-ethoxy)-naphthalenes and bis-(2-hydroxypropoxy)-naphthalenes, bis-(hydroxyethoxy)-phenyl-alkanes and bis-(hydroxypropoxy-phenyl)-alkanes. Cycloaliphatic alcohols may also be mentioned, such as, for example, cyclohexane-1,2-diol, cyclohexane-1,4-diol and 1,4-bis-hydroxymethylcyclohexane. Polyglycols may also be mentioned; for example diethylene glycol, triethylene glycol, tetraethylene glycol, pentaethylene glycol, polyethylene glycol, di-propylene glycol and tri-, tetra-, penta- and poly-propylene glycol, and epoxides, such as ethylene oxide, propylene oxide, butylene oxide and epichlorohydrin.

Of these compounds, those which are particularly preferred are: ethane-1,2-diol, propane-1,2-diol, propane-1,3-diol, butane-1,2-diol, butane-1,3-diol, butane-2,3-diol, butane-1,4-diol, 3-chloropropane-1,2-diol, hexane-1,6-diol, glycerol, tris-hydroxymethylpropane, diethanolamine, triethanolamine, bis-(2-hydroxyethoxy)-benzene, bis-(2-hydroxyethoxydiphenyl)-propane, cyclohexanediol, diethylene glycol, triethylene glycol, tetraethylene glycol, ethylene oxide, propylene oxide and epichlorohydrin.

Examples of compounds of groups 2 are: malonic acid, succinic acid, glutaric acid, adipic acid, pimelic acid, suberic acid, azelaic acid, sebacic acid, fumaric acid, maleic acid, methylenemalonic acid, ethylidenemalonic acid, glutaconic acid, itaconic acid, mesaconic acid, citraconic acid, muconic acid, hex-2 (or -3)-ene-dioic acid, acetylenedicarboxylic acid, phthalic acid, isophthalic acid, terephthalic acid, biphenyldicarboxylic acid, binaphthyldicarboxylic acid, naphthalenedicarboxylic acids, cyclohexanedicarboxylic acids, 5-norbornene-2,3-dicarboxylic acid, di-halogenosuccinic acid, sulphosuccinic acid, phosphonosuccinic acid and their acid anhydride forms and acid halide forms and ester.

Of these, there may be mentioned, in particular; maleic anhydride, phthalic anhydride, succinic anhydride, malonic acid, glutaric acid, adipic acid, sebacic acid, fumaric acid, isophthalic acid, terephthalic acid, terephthalic acid dimethyl ester, cyclohexane-1,4-dicarboxylic acid and sulphosuccinic acid.

Examples of compounds of group 3 are: phosphoric acid, in the form of an aqueous solution or in the syrupy or crystalline form, polyphosphoric acid, metaphosphoric acid, phosphorus pentoxide, $POCl_3$, $P_2O_3Cl_4$ and $PCl_5$. Of these, phosphoric acid, in the crystalline or syrupy form or in the form of an aqueous solution, polyphosphoric acid, $P_2O_5$ and $POCl_3$ are preferred.

The compounds of group 2 can be in the molar ratio (0 to 20):1 to those of group 3, preferably in the ratio (0.05 to 10):1 and particularly preferably in the ratio (0.1 to 4):1. A preferred ratio of compounds of the groups 1:2:3 of 1:(0.04 to 1.2):(0.07 to 1.3) and a particularly preferred ratio of 1:(0.2 to 0.8):(0.2 to 1.2) results from this.

The phosphoric acid esters according to the invention are water-soluble esters, in particular polyesters of the formula (III):

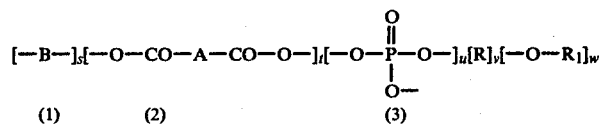
(III)

wherein
R denotes a hydrogen ion, an alkali metal ion or an equivalent of an alkaline earth metal ion, or ammonium of the formula

wherein
$R_2$ = hydrogen, $C_1$–$C_{14}$-alkyl, preferably $C_1$–$C_6$-alkyl, which can be substituted by hydroxyl, or phenyl-$C_1$–$C_6$-alkyl, which can be substituted by methyl in the phenyl ring, and
$R_1$ denotes hydrogen or $C_1$–$C_6$-alkyl, preferably hydrogen,
A has the meaning indicated in formula (II),
B has the meaning indicated in formula (I) and
the quantities s, t, u, v and w indicate the ratios of the number of mols,
with the following provisos:
1. s is ⅔ (t+u) to 3/2 (t+u), preferably ¾ (t+u) to 4/3 (t+u),
2. v is equal to or greater than (2t+3u)−(2s),
3. the structural elements (2) are not linked directly with (3) or to one another,
4. one or more structural elements (3) can be linked in a pyrophosphate-like manner; compounds without pyrophosphate bonds are preferred,
5. the structural elements (3) can be in the form of monoesters, diesters or triesters; monoesters and diesters are preferred,
6. two structural elements (1) are always linked to one another via a structural element (2) and/or (3),
7. the radicals R belong to a structural element (2) and/or (3),
8. the radicals O—$R_1$ are bonded to a structural element (1) and
9. w is between 0 and ⅔ s, preferably between 0 and ½ s.

Of the phosphoric acid esters of the formulae (III), those of the formula

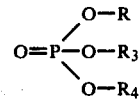

wherein
R has the abovementioned meaning,
$R_3$ represents —B—X,
wherein
B has the abovementioned meaning and
X represents OH,

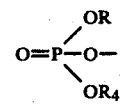

or —O—CO—A—COO—Y and
Y denotes hydrogen,

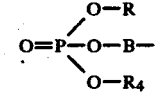

or —B—OH and
A has the abovementioned meaning, and
$R_4$ represents R or $R_3$, are preferred.

The molar ratio is preferably that indicated above.

The phosphoric acid esters of the formula (III) are prepared by any desired linking of the structural elements (1), (2) and (3), which, in each case, can be identical or different, the above provisos applying.

In a particularly preferred embodiment, the alcohols (I) and the carboxylic acids (II) are reacted with orthophosphoric acid. In this procedure, the orthophosphoric acid can be employed in the crystalline or syrupy form or in the form of a concentrated aqueous solution, for example in a 40 to 90% strength solution.

For example, the orthophosphoric acid can first with the alcohols (I) to give compounds of the formula

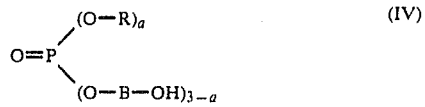

wherein
R and B have the abovementioned meaning,
a is 1 or 2 and
R is preferably H,
according to known processes.

The compound (IV) is then reacted with 0 to 1 mol of phosphoric acid, preferably without further phosphoric acid, and with 0.05 to 9 mols of carboxylic acid (II), preferably 0.1 to 6 mols, and with 0 to 9 mols of alcohol (I), preferably with 0 to 6 mols, the numbers of mols in each case being calculated relative to one mol of the compound (IV). The sum of the numbers of mols of the diol (I) employed in the synthesis of the compound (IV) and of the diol (I) employed in the further reaction is $\frac{2}{3}$ to 3/2, preferably $\frac{3}{4}$ to 4/3 of the sum of the numbers of mols of phosphoric acid (or derivative) employed and dicarboxylic acid (II) employed. The reaction takes place at 120° to 260° C., preferably at 150° to 200° C., optionally in vacuo, the water of reaction distilling over and the ester (III) forming. It is also possible to first react the carboxylic acid (II) with the alcohols (I) to give the esters (V)

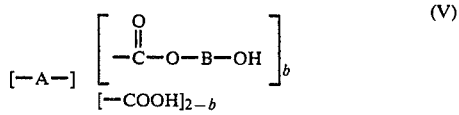

wherein
A and B have the abovementioned meaning and
b is 1 or 2.

The reaction takes place according to processes which are in themselves known, under acid catalysis by, for example, mineral acids, such as $H_3PO_4$, HCl or $H_2SO_4$, or by compounds such as p-toluenesulphonic acid, Lewis acids, light metal oxides and heavy metal oxides or light metal salts and heavy metal salts, such as, for examle, halides. The water of reaction is distilled off.

The compounds (V) then react with orthophosphoric acid (which may be in the salt form) and/or the compounds (IV) and optionally alcohols (I) in the molar ratio 1:(0.05 to 25):(0.05 to 25):(0–25), in particular in the molar ratio 1:(0.25 to 10):(0.25 to 10):(0–10). The sum of the numbers of mols of the diol (I) employed in the synthesis of the compound (V) and of the diol (I) employed in the further reaction is $\frac{2}{3}$ to 3/2, preferably $\frac{3}{4}$ to 4/3, of the sum of the numbes of mols of dicarboxylic acid (II) employed and phosphoric acid employed. The reaction is effected at temperatures from 120° to 260° C., preferably from 150° to 200° C. to give the esters (III), the water of reaction being distilled off, if necessary in vacuo.

A procedure in which compounds of the formula (V) in which b is 2 are reacted with 0.25 to 10 mols of orthophosphoric acid, calculated relative to one mol of (V), is preferred.

It is also possible to react compounds (V) (b=1) with compounds (IV) (a=1) in the abovementioned ratio.

Furthermore, it is possible to react compounds (V) (in which b=1) and orthophosphoric acid and the alcohol (I) in the abovementioned molar ratio.

A preferred procedure furthermore consists in simultaneously reacting orthophosphoric acid, alcohols (I) and carboxylic acids (II) in the molar ratio (0.07 to 1.3):(0.04 to 1.2), preferably (0.2 to 1.2):1:(0.2 to 0.8), the sum of the numbers of mols of orthophosphoric acid and dicarboxylic acid (II) being $\frac{2}{3}$ to 3/2, preferably $\frac{3}{4}$ to 4/3, of the number of mols of the alcohol (I). In this procedure, formation of the monoesters or diesters of the compounds of the (IV) and (V) type is first effected by regulating the temperature and pressure such that the compounds (I) and (II) do not boil or decompose, and the mixture is then later warmed, preferably to 150° to 200° C., and the esterification is brought to completion, optionally in vacuo.

All the esterification reactions described are acid-catalysed, the orthophosphoric acid participating in the reaction or the compound (IV) serving as the catalyst in the simplest and preferred case. It is also possible to use other catalysts, for example mineral acids, such as $H_2SO_4$ and HCl, and furthermore organic sulphonic acids, for example toluenesulphonic acid, or also Lewis acids, such as heavy metal oxides and light metal oxides and heavy metal salts and light metal salts, for example halides.

The compounds (I), (II), (IV) or (V) employed are preferably themselves used as the reaction medium, or a solvent which does not participate in the reaction is added, for example an aliphatic or aromatic hydrocarbon, such as petroleum ether, benzene, toluene or xylene.

It is also possible to use a halogenohydrocarbon, for example methylene chloride, chloroform, carbon tetrachloride, trichloroethylene, perchloroethylene, chlorobenzene, dichlorobenzene or chlorotoluene. Polar, aprotic solvents can also be used as the reaction medium, for example dimethylformamide, acetonitrile, ether or dioxane.

The water or reaction is either removed by distillation, optionally in vacuo, or by azeotropic distillation, it being possible for one of the abovementioned media to be used as the entraining agent, as long as it is water-immiscible. Xylene, perchloroethylene and dichlorobenzene are preferred.

Instead of free orthophosphoric acid or the free carboxylic acid (II), the activated forms of these acids can also be very advantageously employed in the reactions described above for the preparation of the compounds (IV) and (V) and their further esterification to (III). Such activated forms which may be mentioned are, in particular, the acid anhydrides, for example all the possible dehydrated forms of phosphoric acid, that is to say anhydrous orthophosphoric, pyrophosphoric, polyphosphoric and metaphosphoric acid and phosphorus pentoxide, as well as various anhydride forms of the carboxylic acids (II), for example intramolecular or intermolecular anhydrides.

A preferred process consists in first synthesising the compounds (IV) from one of the dehydrated forms of phosphoric acid mentioned, and reacting this compound in a further reaction step with alcohols (I) and anhydrides, of the abovementioned type, of the carboxylic acids (II), with heating and in vacuo, to give the polyesters (III). In this procedure, the reaction conditions for the reaction of the alcohols (I) with the dehydrated forms of orthophosphoric acid are maintained such that a homogeneous mixture is formed from the reactants at as low as possible a temperature, which indicates the formation of compounds of the (IV) type. Since the reaction with phosphorus pentoxide sometimes proceeds very energetically, a diluent, for example toluene, cresol, perchloroethylene, acetonitrile or mono- or di-chlorobenzene, in which the phosphorus pentoxide is initially suspended, is advantageously used here. The alcohol (I) is then added dropwise to, or allowed to run into, the suspension. It can also be advantageous to add the carboxylic acids (II) or their anhydrides, if necessary in portions, to the suspension and then to allow the alcohol (I) to run in or to add it dropwise. The compounds (IV) which have been formed from the dehydrated forms of phosphoric acid or form ordinary orthophosphoric acid can then be reacted with anhydrides, of the type mentioned, of carboxylic acids (V) and optionally further alcohol (I) and converted into polyesters. For this, the reactants are heated in vacuo to 120° to 260° C., preferably 150° to 200° C., water of reaction distilling off.

A preferred procedure furthermore consists in synthesising the compounds (V), in which b is preferably 2, from the anhydrides of the carboxylic acids (II) and from the alcohols (I), optionally under acid-catalysis using one of the catalysts mentioned, and reacting these compounds (V) further with H3PO4 or the dehydrated forms thereof and optionally with further alcohol (I). The polyesters (III) are formed here, optionally after converting the alcohols (I) into the monoester stage, by applying a vacuum and heating the reactants, preferably to 150° to 200° C.

Instead of the phosphoric acid anhydrides or the anhydrides of the carboxylic acid (II), it is also possible to employ the corresponding phosphoric acid halides, for example POCl3, P2O3Cl4 or PCl5, or the carboxylic acid halides, especially the chlorides.

The phosphoric acid esters (IV) can also be prepared from phosphoric acid or one of its primary or secondary salts, for example the alkali metal salt, alkaline earth metal salt or ammonium salt, and alkylene oxides, for example ethylene oxide, propylene oxide or epichlorohydrin. Such processes are known from the literature (Chem. Phar.-Bull. 5, 121–215; (1957)). Correspondingly, it is also possible to prepare the compounds (V) from the carboxylic acids and the alkylene oxides (German Pat. No. 905,736).

Examples which may be mentioned of the compounds (IV) which can be prepared by one of the processes described above are, in particular, the phosphoric acid mono-esters and bis-esters of the following alcohols (II): glycol, propane-1,2-diol, propane-1,3-diol, butane-1,4-diol, butane-1,3-diol, 3-chloropropane-1,2-diol, pentane-1,5-diol, hexane-1,6-diol, 2-butane-1,4-diol, 2-hydroxymethyl2-propen-1-ol, glycerol, methyldiethanolamine, ethyldiethanolamine, triethanolamine, 1,2-bis-2-(hydroxyethoxy)-benzene, 1,4-bis-2-(hydroxyethoxy)-benzene, 4,4'-bis-(2-hydroxyethyl)-diphenyl sulphone, bis-(2-hydroxyethoxyphenyl)-ethane, bis(2-hydroxyethoxyphenyl)-propane, cyclohexane-1,4-diol, diethylene glycol, triethylene glycol, tetraethylene glycol, pentaethylene glycol, dipropylene glycol, tripropylene glycol, tetrapropylene glycol and pentapropylene glycol.

Monoesters and diesters of the compounds (V) which should be mentioned in particular are formed from the abovementioned alcohols and the following carboxylic acids (II): malonic acid, succinic acid, maleic acid, fumaric acid, glutaric acid, methylenemalonic acid, adipic acid, glutaconic acid, itanonic acid, mesaconic acid, citraconic acid, muconic acid, acetylenedicarboxylic acid, phthalic acid, terephthalic acid, cyclohexanedicarboxylic acid, sulphosuccinic acid, phosphonosuccinic acid and dimethyl ether-α,α'-dicarboxylic acid, and pimelic, suberic, azelaic and sebacic acid.

The polyesters (III) can furthermore be prepared in the following manner: phosphoric acid and/or the carboxylic acid (II) are each converted into the corresponding chlorohydrin esters (IV) and/or (V) using epichlorohydrin or its derivatives. These esters then react further with bases or aqueous alkali to give the glycidyl esters and are reacted directly with further carboxylic acid (II) and/or phosphoric acid to give the polyesters (III).

It is also possible to react the chlorohydrin esters (IV) and/or (V) with salts, preferably alkali metal salts or alkaline earth metal salts, of the carboxylic acids (II) and/or of phosphoric acid to give the polyesters (III).

Instead of the alcohols (I), it is also possible to employ their derivatives of the formula

Y—B—Y wherein
B has the abovementioned meaning and
Y represents a group which can be replaced nucleophilically, for example halogen, such as Cl, Br or I, tosylate or methanesulphonate.

The two groups Y can be identical or different. One of the groups Y can also be a hydroxyl group.

The polyesters (I) can also be prepared by transesterification, the phosphoric acid and/or the carboxylic acids (II) being employed in the form of esters of highly volatile alcohols, for example methanol, ethanol, isopropanol, propanol or 2-ethylhexanol. This transesterification can be acid-catalysed or alkali-catalysed. Amongst the esters which can be employed, there may be mentioned, in particular, terephthalic acid dimethyl ester.

After a reaction time of up to 48 hours, preferably up to 15 hours, the polyesters (III) prepared in the ways described above, are obtained as yellowish- to brown-coloured products which, when not, can be stirred or are highly viscous and are solid when cold. They can be isolated in the pure form, for example by pouring out and cooling the hot mass, or solutions can be prepared, for example in organic solvents or preferably in water. In order to dissolve the substances in water, preferably one to five times their weight of water is added and the mixture is neutralised with a base or aqueous alkali, preferably with alkali metal hydroxide solution or alkaline earth metal hydroxide solution, in a manner such that the pH value does not exceed 8. For solution, the best procedure is to cover the polyester (I), which is at the bottom of the reaction vessel and has solidifed, with the calculated amount of H2O, to stir this water continuously and to keep the pH value at 5 to 8 by adding small amounts of concentrated sodium hydroxide solution, whilst warming the mixture to 20° to 50° C. The polyester (I) thereby dissolves. Finally, the pH value is preferably adjusted to 5 to 7, 20 to 50% strength solutions being obtained. The aqueous solutions can be evaporated to give dry powders.

The molecular weight of the compounds (III) is 300 to 10,000. As a result, the carboxylic acids (II) are bonded to two mols of the alcohols (I); a certain proportion of orthophosphoric acid is likewise linked, on two P—OH groupings, with the alcohols (I) to give phosphoric acid esters. A further proportion of the phosphoric acid has the monoester structure, and only a small proportion may be in the form of a phosphoric acid triester. Accordingly, the IR spectrum shows the absorption bands corresponding to the carboxylic acid esters at 1,730 to 1,800 nm and the bands corresponding to the P—O—C bonds of the phosphoric acid esters at 1,020 to 1,120 nm. A certain small proportion of the phosphoric acid can also be bonded in a pyrophosphate-like or polyphosphate-like manner via a P—O—P bond.

The polycondensates can consist of the alternating structural elements (1) and (3), and structural elements (2) can also be co-condensed. The compounds of the formula (II) and (V) thus fulfil two functions: on the one hand, they contribute to the effect of the compounds (III), and on the other hand they have a catalytic effect on the esterification of the phosphoric acid groups—P—OH (if these are employed in the reaction or are formed in the course of the reaction) with the diols of the formula (I). This catalysis consists of transesterification, since the phosphoric acid esters are formed from the carboxylic acid esters. Thus, in the course of the reaction, as the reaction increases escape of the dicarboxylic acid from the reaction mixture is observed, for example maleic anhydride or phthalic anhydride sublimes out.

The water-solubility of the compounds results from the fact that, the phosphoric acid molecules, as a rule one, or in some cases two, P—OH groupings are present in the free form and confer water-solubility on the compounds, either directly or after deprotonation with bases or aqueous alkalis.

In the esterification reactions described above, some side reactions can also take place, for example etherification or elimination reactions on the alcohols (I). If the reaction is carried out properly, these reactions do not become too powerful and do not prevent the synthesis of the polyesters (III).

The discolorations of brown to black which frequently occur during the esterification with phosphoric acid can be largely prevented by adding reducing agents, preferably derivatives of low-valency phosphorus, for example $H_3PO_3$ or its salts.

The compounds (III) are resistant towards hydrolysis and are stable in aqueous solutions for several months; after boiling in water at pH 7 for ten hours, they do not noticeably lose their activity. However, the ester bonds are attacked by bacteria, so that the compounds (III) are biologically degradable.

The compounds (III) are used as dispersing agents for organic and inorganic substances, preferably in an aqueous medium. They are preferably used as dispersing agents for dyestuffs and pigments.

They can be used for the preparation of finished dyestuffs or for dispersing dyestuffs in a dyebath.

They can also be used as emulsifiers for organic substances in water and as levelling agents in the dyeing industry, for example in the dyeing of polyester fibres.

Furthermore, the compounds (III) can be used for the "liquefaction" of concentrated mixtures of organic or inorganic solids and water. The "liquefaction" of these mixtures consists in lowering the viscosity until they can be easily stirred and poured. Examples of solids which may be mentioned are organic dyestuffs, inorganic pigments, for example metal oxides, cement and concrete.

In addition, they can be employed, instead of polyphosphates, as builders in detergents.

EXAMPLE 1

47 g of phosphorus pentoxide and 33 g of $H_3PO_4$ are mixed in a reaction flask, whilst heating for a short time, and the mixture is cooled and 124 g of glycol and 1 g of crystalline sodium hypophosphite are added. The mixture is slowly heated to 180° C., whilst stirring, and about 35 g of an aqueous liquid are distilled off in the course of 3 hours. After renewed cooling, 98 g of maleic anhydride are added and a further 10 g of liquid are distilled off at temperatures from 190° to 200° C. in the course of 6 hours, under a slowly increasing vacuum. The hot melt is allowed to cool and covered with a layer of 1 l of water. The aqueous layer is stirred and 50% strength sodium hydroxide solution is added dropwise such that the pH value remains at 5–8. Finally, the pH is adjusted to 5–6. An approximately 20% strength solution is obtained.

EXAMPLE 2

71 g of phosphorus pentoxide and 98 g of maleic anhydride, together with 3 g of phosphorous acid, are dissolved or suspended in about 200 g of perchloroethylene and 124 g of glycol are then slowly added dropwise at 80° C. The mixture is subsequently stirred under reflux for some hours and then distilled. The residue which remains in the flask is dissolved with $H_2O$ and concentrated sodium hydroxide solution to give a 40% strength solution of pH 5 to 6.

EXAMPLE 3

30 g of polyphosphoric acid (82% of $P_2O_5$) and 100 g of maleic acid bis-(hydroxyethyl) ester are heated to 160° C. for 5 to 6 hours, whilst stirring, and the aqueous liquid is distilled off in vacuo. The residue is then dissolved with $H_2O$ and concentrated sodium hydroxide solution to pH 5 to 6 to give a 20% strength solution.

EXAMPLE 4

100 g of maleic acid bis-(hydroxyethyl) ester and 57 g of $H_3PO_4$, 85% strength in $H_2O$, as well as 3 g of phosphorous acid are heated to 185° to 195° C. in a reaction flask over a period of 12 hours. About 30 g of an aqueous liquid thereby distill off. Towards the end of the reaction, an increasingly higher vacuum is applied and a 28% strength solution of pH 5 to 6 is prepared with $H_2O$ and concentrated sodium hydroxide solution.

EXAMPLE 5

47 g of glycerol, 41 g of polyphosphoric acid (82% of $P_2O_5$) and 1 g of phosphorous acid are stirred at 120° C. for 30 minutes, the mixture is then cooled and 74 g of phthalic anhydride are added, and the mixture is heated again to 150° C., under a slowly increasing vacuum, an aqueous liquid distilling off. After about 14 hours at 150° C., the residue is dissolved in the cold with $H_2O$ and concentrated sodium hydroxide solution to give a 35% strength solution of pH 5 to 6.

EXAMPLE 6

31 g of glycol, 44 g of phthalic anhydride and 10 g of maleic anhydride are heated to 120° to 130° C. under 200 mm Hg, whilst stirring, $H_2O$ distilling off. After 1.5 hours, 17 g of $H_3PO_4$ are added and the mixture is gradually heated up to 180° to 190° C. under an increasing vacuum in the course of 10 hours, whilst distilling further. A 40% strength solution of pH 5 to 6 is prepared by adding H$_2$O and concentrated sodium hydroxide solution.

EXAMPLE 7

15.5 g of glycol, 23.4 g of glycerol, 74 g of phthalic anhydride and 29 g of H$_3$PO$_4$, 85% strength, are slowly heated to 180° to 190° C. under an initially low and later higher vacuum in the course of 8 hours, whilst stirring, an aqueous liquid distilling off. An aqueous solution is prepared with H$_2$O and concentrated sodium hydroxide solution.

EXAMPLE 8

49 g of maleic anhydride and 76 g of propane-1,3-diol are heated to 90° C. for 30 minutes, whilst stirring. 58 g of 85% strength H$_3$PO$_4$ and 2 g of phosphorous acid are then added. A vacuum of 200 mm Hg is applied and the mixture is heated to 180° C. at intervals of 10° to 20° C. per hour, whilst distilling off an aqueous liquid, and is further stirred for some time at 180° to 190° C., the vacuum is slowly increased and then, after cooling, a 25% strength solution of pH 5 to 6 is prepared with H$_2$O and concentrated sodium hydroxide solution.

EXAMPLE 9

49 g of maleic anhydride and 90 g of butane-1,3-diol are stirred at 90° C. for some time and 58 g of 85% strength H$_3$PO$_4$ and 2 g of phosphorous acid are then added. The mixture is heated to 170° to 190° C. at 10° to 20° C. per hour in vacuo, whilst distilling off an aqueous liquid, and is further kept at this temperature for some hours. A 20% strength solution of pH 6 to 7 is then prepared with H$_2$O and concentrated sodium hydroxide solution.

EXAMPLE 10

49 g of maleic anhydride and 76 g of propane-1,2-diol are heated at 90° C. for some minutes, whilst stirring, and 58 g of 85% strength H$_3$PO$_4$ and 2 g of phosphorous acid are then added. The mixture is heated to 170° to 190° C. at intervals of 10° to 20° C. per hour under an initially low and later higher vacuum, an aqueous liquid distilling off. The mixture is further stirred at 170° to 180° C. for some hours and then, after cooling, the residue is dissolved with H$_2$O and concentrated sodium hydroxide solution to give a 20% strength solution of pH 5 to 6.

EXAMPLE 11

49 g of maleic anhydride and 118 g of hexane-1,6-diol are stirred at 90° C. for some minutes and 58 g of 85% strength H$_3$PO$_4$ and 2 g of phosphorous acid are then added. The mixture is heated to 170° to 190° C. at intervals of 10° to 20° C. per hour under an initially relatively low and later higher vacuum, an aqueous liquid distilling off. The mixture is further stirred and further distilled at 170° to 180° C. for some hours and then, after cooling, the residue is dissolved with H$_2$O and concentrated sodium hydroxide solution to give a 25% strength solution of pH 5 to 6.

EXAMPLE 12

49 g of maleic anhydride and 106 g of diethylene glycol are stirred at 90° C. for some minutes and 58 g of 85% strength H$_3$PO$_4$ and 2 g of phosphorous acid are then added. The mixture is heated to 170° to 190° C. at intervals of 10° to 20° C. per hour under an initially low and later higher vacuum, an aqueous liquid distilling off. The mixture is further stirred and further distilled at 170° to 180° C. for some hours and then, after cooling, a 25% strength solution of pH 5 to 6 is prepared with H$_2$O and concentrated sodium hydroxide solution.

EXAMPLE 13

49 g of maleic anhydride and 149 g of triethanolamine are stirred at 90° C. for some minutes and 58 g of 85% strength phosphoric acid and 2 g of phosphorous acid are then added. The mixture is heated to 170° to 190° C. at intervals of 10° to 20° C. per hour under an initially low and later higher vacuum, an aqueous liquid distilling off. The mixture is further stirred and further distilled at 170° to 180° C. for some hours and then after cooling, a 25% strength solution of pH 6 to 7 is prepared with H$_2$O and concentrated sodium hydroxide solution.

EXAMPLE 14

49 g of maleic anhydride and 150 g of triethylene glycol are stirred at 90° C. for some minutes and 58 g of 85% strength phosphoric acid and 2 g of phosphorous acid are then added. The mixture is slowly heated to 170° to 190° C. under an initially low and later higher vacuum and kept under these conditions for some hours and an aqueous liquid is distilled off. After cooling, a 25% strength solution of pH 5 to 6 is prepared with H$_2$O and concentrated sodium hydroxide solution.

EXAMPLE 15

49 g of maleic anhydride and 194 g of tetraethylene glycol are stirred at 90° C. for some minutes and 58 g of 85% strength phosphoric acid and 2 g of phosphorous acid are then added. The mixture is slowly heated to 170° to 190° C. under an initially low and later higher vacuum and kept under these conditions for some hours and an aqueous liquid is distilled off. After cooling, a 25% strength solution of pH 5 to 6 is prepared with H$_2$O and concentrated NaOH.

EXAMPLE 16

49 g of maleic anhydride and 116 g of cyclohexane-1,4-diol are stirred at 90° C. for some minutes and 58 g of 85% strength phosphoric acid and 2 g of phosphorous acid are then added. The mixture is slowly heated to 170° to 190° C. under an initially relatively low and later higher vacuum and kept under these conditions for some hours and an aqueous liquid is distilled off. After cooling, a 25% strength solution of pH 5 to 6 is prepared with H$_2$O and concentrated sodium hydroxide solution.

EXAMPLE 17

49 g of maleic anhydride and 62 g of glycol are stirred at 90° C. for some minutes and 58 g of 85% strength phosphoric acid and 2 g of phosphorous acid are then added. The mixture is slowly heated to 170° to 190° C. under an initially relatively low and later higher vacuum and is kept under these conditions for some hours and an aqueous liquid is distilled off. A 50% strength solution of pH 7 is prepared with H$_2$O and concentrated sodium hydroxide solution, 128 g of 40% strength NaHSO$_3$ solution is added to this solution and the mixture is heated to the reflux for 5 hours. The solution formed is about 43% strength.

EXAMPLE 18

66 g of glutaric acid and 62 g of glycol are stirred at 90° C. for some minutes and 58 g of 85% strength phosphoric acid and 2 g of phosphorous acid are added to the mixture. The mixture is slowly heated to 180° to 190° C. under an initially relatively low and later higher vacuum and is kept under these conditions for some hours and an aqueous liquid is distilled off. A 25% strength solution is prepared with $H_2O$ and concentrated sodium hydroxide solution.

EXAMPLE 19

73 g of adipic acid and 62 g of glycol are stirred at 90° C. for some minutes and 58 g of 85% strength phosphoric acid and 2 g of phosphorous acid are then added. The mixture is slowly heated to 180° to 190° C. under an initially low and later higher vacuum and is kept under these conditions for some hours, an aqueous liquid distilling off. After cooling, a 20% strength solution of pH 6 to 7 is prepared with $H_2O$ and concentrated sodium hydroxide solution.

EXAMPLE 20

52 g of malonic acid and 62 g of glycol are stirred at 90° C. for some minutes and 58 g of 85% strength phosphoric acid and 2 g of phosphorous acid are then added. The mixture is heated to 180° to 190° C. under an initially low and later higher vacuum, an aqueous liquid distilling off and the mixture being kept under these conditions for some hours. A 20% strength solution of pH 6 to 7 is prepared with $H_2O$ and concentrated sodium hydroxide solution.

EXAMPLE 21

50 g of succinic anhydride and 62 g of glycol are stirred at 90° C. for some minutes and 58 g of 85% strength phosphoric acid and 2 g of phosphorous acid are then added. The mixture is heated to 180° to 190° C. under an initially low and later higher vacuum, an aqueous liquid distilling off and the mixture being kept under these conditions for some hours. A 20% strength solution of pH 6 to 7 is prepared with $H_2O$ and concentrated sodium hydroxide solution.

EXAMPLE 22

100 g of cyclohexanedicarboxylic acid and 62 g of glycol are stirred at 90° C. for some minutes and 58 g of 85% strength phosphoric acid and 2 g of phosphorous acid are then added. The mixture is heated to 180° to 190° C. under an initially low and later higher vacuum and is kept under these conditions for some hours, an aqueous liquid distilling off. A 20% strength solution of pH 6 to 7 is prepared with $H_2O$ and concentrated sodium hydroxide solution.

EXAMPLE 23

38 g of polyphosphoric acid (82% of $P_2O_5$), 1 g of triethanolamine and 2 g of phosphorous acid are brought together and heated to 80° C. for 30 minutes. 29 g of propylene oxide are added dropwise in the course of 30 minutes and the mixture is stirred for a further 6 hours at 100° C. A 20% strength solution of pH 5 to 6 is prepared with $H_2O$ and concentrated sodium hydroxide solution.

EXAMPLE 24

116 g of 85% strength phosphoric acid, 60 g of glycol and 5 g of maleic anhydride as well as 2 g of phosphorous acid are heated to 120°–130° C., whilst stirring, $H_2O$ distilling off, and then further heated to 180°–190° C. and an initially low and later higher vacuum is applied. An aqueous liquid distils off. A 30% strength solution of pH 6–7 is prepared with $H_2O$ and concentrated sodium hydroxide solution.

EXAMPLE 25

116 g of 85% strength phosphoric acid, 60 g of glycol and 7.3 g of adipic acid as well as 2 g of phosphorous acid are heated to 120°–130° C. in a flask, whilst stirring, $H_2O$ distilling off, and then brought to 180°–190° C. and an initially low and later higher vacuum is applied. An aqueous liquid distils off. A 30% strength solution of pH 6 to 7 is prepared with $H_2O$ and concentrated sodium hydroxide solution.

EXAMPLE 26

400 ml of $H_2O$ at 50° C., which contains 1 g/l of the substances prepared in Examples 1 to 25, are poured over 0.8 g of Disperse Red 106, whilst stirring, and the mixture is brought to the boil for 10 minutes. It is then filtered through a circular filter in vacuo. The paper filter remains clear and shows no agglomerisation of the dyestuff.

We claim:

1. A method of dispersing organic or inorganic substances in an aqueous medium and of emulsifying organic substances in an aqueous medium comprising incorporating together with said inorganic or organic substances in water, a water-soluble phosphoric acid ester prepared at 80° to 100° C. from a polyol and/or epoxide and a phosphoric acid or a derivative thereof in the molar ratio 1:0.05 to 1.5 or prepared at 120° to 260° C. from a polyol and/or epoxide, a polycarboxylic acid or derivative thereof and a phosphoric acid or a derivative thereof in the molar ratio of $1:\leq 1.5:0.05–1.5$, the sum of the number of mols of the acids being ⅔ to 3/2 of the number of mols of the alcohols, the esters being employed in an amount sufficient to effect dispersion and emulsification.

2. The method of claim 1, wherein the substance to be dispersed is a dyestuff or pigment.

3. The method of claim 1 wherein the phosphoric acid ester is prepared from (a) a polyhydric, saturated or unsaturated, aliphatic, cycloaliphatic, aromatic or araliphatic alcohol which has 2 to 26 C atoms and is unsubstituted or substituted by halogen, amino or sulpho; and/or (b) a polyhydric alcohol which is formed by etherifying one or more of said polyhydric alcohols with one another or by ethoxylating and/or propoxylating one or more of said polyhydric alcohols; and/or (c) a 1,2-epoxide or 1,3-epoxide; and (d) optionally a saturated or unsaturated aliphatic, cycloaliphatic, aromatic or araliphatic carboxylic acid which has 2 to 26 C atoms and contains at least two COOH groups, and optionally contains hydroxyl, ether, halogen, amino, sulpho, or phosphonic acid groups, and functional derivatives thereof; and (e) phosphoric acid or its anhydrides, halides or oxyhalides.

4. The method of claim 3 wherein the ester is prepared in the presence of a reducing agent.

5. The method of claim 3 wherein the ester is prepared during a reaction time of up to 48 hours.

6. The method of claim 3, wherein the phosphoric acid ester is a polyester of the formula:

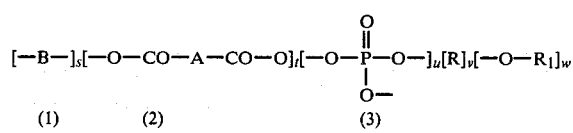

(1)    (2)    (3)

wherein

R is a hydrogen ion, an alkali metal ion, or an equivalent of an alkaline earth metal ion, or ammonium of the formula

wherein $R_2$ is hydrogen, $C_1$-$C_{14}$-alkyl which can be substituted by hydroxyl, or phenyl-$C_1$-$C_6$-alkyl, which can be substituted by methyl in the phenyl ring; and
$R_1$ is hydrogen or $C_1$-$C_6$-alkyl;
A is $C_1$-$C_{10}$-alkylene,
$C_2$-$C_{10}$-alkenylene or alkinylene, or a phenylene, biphenylene, cyclohexylene or norbornenylene radical; and
the quantities s, t, u, v and w indicate the ratios of the number of mols,
with the following provisos:
1. s is ⅔ (t+u) to 3/2 (t+u);
2. v is equal to or greater than (2t+3u)−(2s);
3. the structural elements (2) are not linked directly with (3) or to one another;
4. one or more structural elements (3) can be linked in a pyrophosphate-like manner;
5. the structural elements (3) are in the form of monoesters, diesters or triesters;
6. two structural elements (1) are always linked to one another via a structural element (2) and/or (3);
7. the radicals R belong to a structural element (2) and/or (3);
8. the radicals O—R are bonded to a structural element (1); and
9. w is between 0 and ⅔ s.

7. The method of claim 6, wherein the phosphoric acid ester is an ester of the formula:

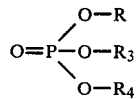

wherein
R represents —B—X;
wherein
X represents OH,

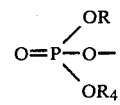

or —O—CO—A—COO—Y and
Y denotes hydrogen,

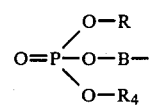

or —B—OH; and
$R_4$ represents R or $R_3$.

8. The method of claim 3 wherein the phosphoric acid ester is prepared from an alcohol of the formula

HO—B—OH wherein
B denotes an alkylene or alkenylene radical with 2 to 10 C atoms, which can be substituted by 1 to 4 hydroxyl groups and/or can be interrupted by Z—N< wherein
Z is $C_1$-$C_4$-alkyl which is optionally substituted by OH; and/or can be interrupted by

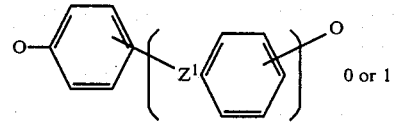

0 or 1 wherein
Z' is $SO_2$ or $C_1$-$C_3$-alkylene; and/or can be interrupted by one of the isomeric phenylene or cyclohexylene radicals;
or B is an isomeric cyclohexylene radical or a radical of the formula

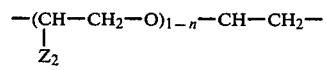

wherein
$Z_2$ is H or $CH_3$; and
n is 50;
and/or 1,2-epoxides or 1,3-epoxides, and optionally a carboxylic acid of the formula

HOOC—A—COOH or its anhydride, acid halide or ester, wherein
A represents alkylene with 1 to 10 C atoms, alkenylene or alkinylene with 2 to 10 C atoms or an isomeric phenylene, biphenylene, cyclohexylene or norbornenylene radical, which can be substituted by $C_1$-$C_4$-alkoxy, sulphone or phosphonic acid groups, and phosphoric acid, its anhydrides, halides or oxyhalides.

9. The method of claim 1 wherein a polycarboxylic acid reactant is employed in addition to the phosphoric acid.

* * * * *